United States Patent
Park et al.

(10) Patent No.: US 12,303,239 B2
(45) Date of Patent: May 20, 2025

(54) APPARATUS FOR ESTIMATING BIO-INFORMATION AND METHOD OF DETECTING ABNORMAL BIO-SIGNAL

(71) Applicant: SAMSUNG ELECTRONICS CO., LTD., Suwon-si (KR)

(72) Inventors: Chang Soon Park, Suwon-si (KR); Ui Kun Kwon, Suwon-si (KR); Young Soo Kim, Suwon-si (KR); Hye Rim Lim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 106 days.

(21) Appl. No.: 18/118,562

(22) Filed: Mar. 7, 2023

(65) Prior Publication Data

US 2024/0081663 A1    Mar. 14, 2024

(30) Foreign Application Priority Data

Sep. 14, 2022    (KR) .................. 10-2022-0115612

(51) Int. Cl.
*A61B 5/021*    (2006.01)
*A61B 5/00*    (2006.01)
*A61B 5/024*    (2006.01)

(52) U.S. Cl.
CPC ...... *A61B 5/02116* (2013.01); *A61B 5/02416* (2013.01); *A61B 5/7221* (2013.01)

(58) Field of Classification Search
CPC ............ A61B 5/02116; A61B 5/02416; A61B 5/7221

See application file for complete search history.

(56) References Cited

U.S. PATENT DOCUMENTS

| | | |
|---|---|---|
| 9,075,446 B2 | 7/2015 | Garudadri et al. |
| 9,136,980 B2 | 9/2015 | Baheti et al. |
| | (Continued) | |

FOREIGN PATENT DOCUMENTS

| | | |
|---|---|---|
| JP | 2013-111467 A | 6/2013 |
| KR | 10-1361578 B1 | 2/2014 |
| | (Continued) | |

OTHER PUBLICATIONS

Lin, W., et al., "Towards accurate estimation of cuffless and continuous blood pressure using multi-order derivative and multivariate photoplethysmogram features," Biomedical Signal Processing and Control. vol. 63, 2021. p. 1-12 (Year: 2021).*

(Continued)

*Primary Examiner* — Sean A Frith
(74) *Attorney, Agent, or Firm* — Sughrue Mion, PLLC

(57) ABSTRACT

An apparatus for non-invasively estimating bio-information and a method of determining whether a bio-signal is normal by the apparatus for estimating bio-information are provided. The apparatus for estimating bio-information according to an embodiment of the disclosure includes: a photoplethysmogram (PPG) sensor configured to measure a PPG signal from an object; and a processor configured to extract a plurality of pairs of local maximum points and local minimum points from a second derivative signal of the PPG signal, to select at least one reference pair from among the extracted plurality of pairs, and to determine whether the PPG signal is normal based on the selected at least one reference pair.

12 Claims, 17 Drawing Sheets

(56) References Cited

U.S. PATENT DOCUMENTS

| | | |
|---|---|---|
| 9,356,731 B2 | 5/2016 | Baheti et al. |
| 9,396,642 B2 | 7/2016 | He et al. |
| 9,396,643 B2 | 7/2016 | He et al. |
| 9,658,825 B2 | 5/2017 | Garudadri et al. |
| 10,687,718 B2 | 6/2020 | Allec et al. |
| 11,660,053 B2 | 5/2023 | Yoon et al. |
| 2015/0112154 A1 | 4/2015 | He et al. |
| 2015/0112155 A1 | 4/2015 | Bijjani et al. |
| 2015/0112156 A1 | 4/2015 | He et al. |
| 2015/0112157 A1 | 4/2015 | Bijjani et al. |
| 2015/0112158 A1 | 4/2015 | He et al. |
| 2015/0112159 A1 | 4/2015 | He et al. |
| 2015/0112208 A1 | 4/2015 | He et al. |
| 2015/0112606 A1 | 4/2015 | He et al. |
| 2015/0164351 A1 | 6/2015 | He et al. |
| 2016/0270668 A1 | 9/2016 | Gil |
| 2017/0325744 A1 | 11/2017 | Allec et al. |
| 2018/0020990 A1 | 1/2018 | Park et al. |
| 2018/0192899 A1 | 7/2018 | Chuang et al. |
| 2018/0289288 A1* | 10/2018 | Kim .................. A61B 5/02108 |
| 2019/0313980 A1* | 10/2019 | Yoon .................... A61B 5/0205 |
| 2020/0268263 A1* | 8/2020 | Lee ........................ A61B 5/681 |
| 2021/0052175 A1 | 2/2021 | Stephens et al. |
| 2021/0100456 A1 | 4/2021 | Park et al. |
| 2021/0353164 A1* | 11/2021 | Chegani ............... A61B 5/0245 |
| 2022/0233079 A1 | 7/2022 | Park et al. |

FOREIGN PATENT DOCUMENTS

| | | |
|---|---|---|
| KR | 10-1503604 B1 | 3/2015 |
| KR | 10-2016-0075677 A | 6/2016 |
| KR | 10-2019-0120684 A | 10/2019 |
| KR | 10-2361725 B1 | 2/2022 |
| KR | 10-2022-0107909 A | 8/2022 |
| WO | 2011/116018 A1 | 9/2011 |
| WO | 2012/034006 A1 | 3/2012 |
| WO | 2012/040957 A1 | 4/2012 |
| WO | 2017/197033 A1 | 11/2017 |

OTHER PUBLICATIONS

Martin C. Baruch et al., "Validation of the pulse decomposition analysis algorithm using central arterial blood pressure", BoiMedical Engineering OnLine, 2014, 20 Pages Total.

Office Action issued Jul. 26, 2024 by the Korean Patent Office for KR Patent Application No. 10-2022-0115612.

* cited by examiner

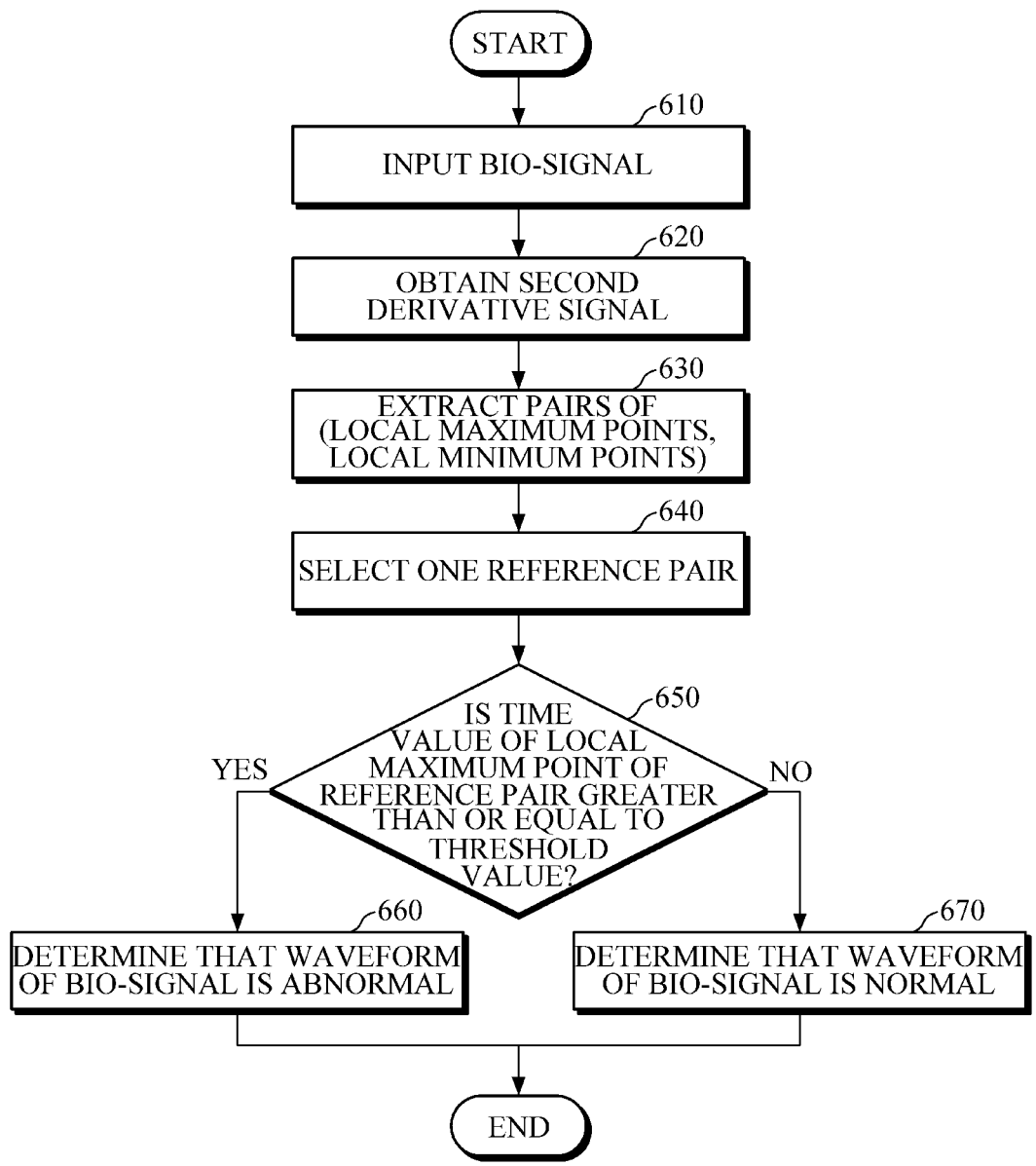

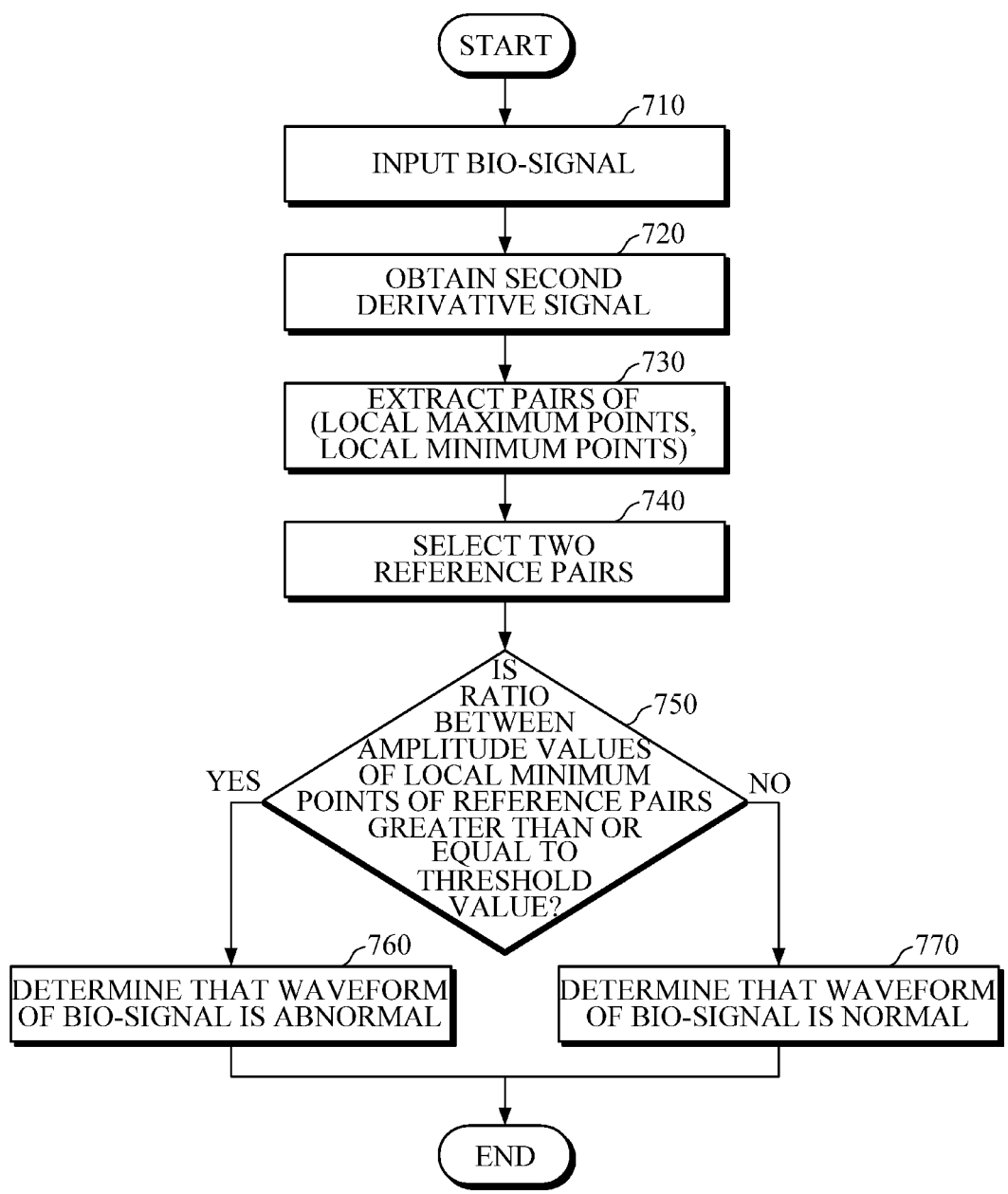

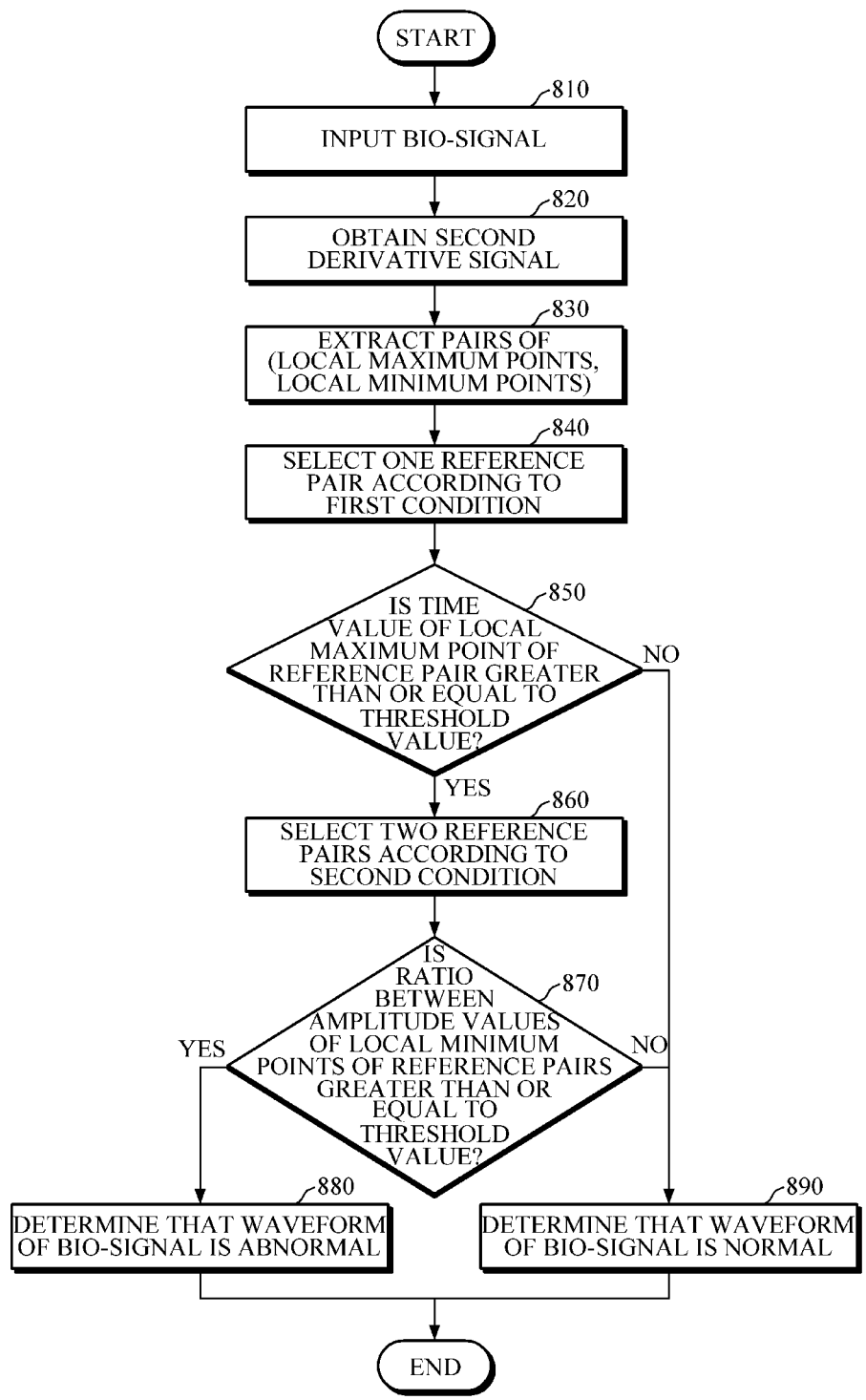

APPARATUS FOR ESTIMATING BIO-INFORMATION AND METHOD OF DETECTING ABNORMAL BIO-SIGNAL

CROSS-REFERENCE TO RELATED APPLICATION(S)

This application claims priority from Korean Patent Application No. 10-2022-0115612, filed on Sep. 14, 2022, in the Korean Intellectual Property Office, the entire disclosure of which is incorporated herein by reference for all purposes.

BACKGROUND

1. Field

The following description relates to an apparatus for non-invasively estimating bio-information and a method of detecting an abnormal bio-signal.

2. Description of the Related Art

Research on information technology (IT)-medical convergence technology, in which IT and medical technology are combined, is being recently carried out to address the aging population, rapid increase in medical expenses, and shortage of specialized medical service personnel. Particularly, monitoring of the health condition of the human body is not limited to a fixed place, such as a hospital, but is expanding to a mobile healthcare sector for monitoring a user's health status at any time and any place in daily life such as at home and office. Electrocardiography (ECG), photoplethysmogram (PPG), and electromyography (EMG) signals are examples of bio-signals that indicate the individual's health condition. A variety of signal sensors are being developed to measure such signals in daily life. Particularly, in the case of a PPG sensor, it is possible to estimate blood pressure of a human body by analyzing a form of pulse wave that reflects a cardiovascular state.

According to a PPG bio-signal related research, the whole PPG signal is a summation of a propagation wave propagating from the heart to peripheral parts of a body and reflection waves returning from the peripheral parts of the body. It is known that information for use in estimating blood pressure can be obtained by extracting various features related to propagation waves or reflection waves.

SUMMARY

In an aspect of an example embodiment, there is provided an apparatus for estimating bio-information, the apparatus including: a photoplethysmogram (PPG) sensor including a light source, configured to emit light toward an object, and a detector, configured to detect light scattered or reflected from the object, the PPG sensor being configured to measure a PPG signal based on the detected light; and a processor configured to obtain a second derivative signal of the PPG signal, configured to extract a plurality of pairs of local maximum points and local minimum points from the obtained second derivative signal, configured to select at least one reference pair from among the extracted plurality of pairs, and configured to determine whether the PPG signal is normal by using the selected at least one reference pair.

Based on a determination that the PPG signal is normal, the processor may be configured to estimate bio-information by using the PPG signal, the bio-information including a blood pressure; and based on a determination that the PPG signal is abnormal, the processor may be configured to determine an estimation failure and terminate estimation of bio-information, or configured to estimate the bio-information after modifying one periodic signal of the PPG signal determined as abnormal, or configured to estimate the bio-information after setting a pair from the selected at least one reference pair as a first pair that is valid for the second derivative signal.

In addition, the apparatus for estimating bio-information may further include an output interface configured to output at least one of a result of the estimation of the bio-information or information about the estimation failure.

The processor may sequentially extract the plurality of pairs of local maximum points and local minimum points from the second derivative signal in a time sequential order.

The processor may obtain a difference between a local maximum value and a local maximum value of each pair of the extracted plurality of pairs, and may select the at least one reference pair based on the obtained difference between the local maximum value and the local maximum value.

The processor may select the at least one reference pair within a predetermined time period which is set based on one cycle of the PPG signal.

The processor may select, as a reference pair, a pair having a largest difference between the local maximum value and the local minimum value, or a pair having a largest value obtained by multiplying the obtained difference between the local maximum value and the local minimum value by a predetermined coefficient.

The processor may compare a time value of a local maximum point of a selected reference pair with a predetermined threshold value, and based on the time value of the local maximum point being greater than the predetermined threshold value, the processor may determine that the PPG signal is abnormal.

Based on a determination that the PPG signal is normal, the processor may set a reference pair as the first pair that is valid for the second derivative signal, and may estimate the bio-information by using at least one of the second derivative signal or the PPG signal.

The processor may select a first pair and a second pair as a first reference pair and a second reference pair, respectively, from among the extracted plurality of pairs.

By using a first amplitude of the PPG signal, which corresponds to a local minimum point of the first reference pair, and a second amplitude of the PPG signal which corresponds to a local minimum point of the second reference pair, the processor may determine whether the PPG signal is normal.

Based on a ratio between the first amplitude and the second amplitude being greater than a predetermined threshold value, the processor may determine that the PPG signal is abnormal.

In an aspect of an example embodiment, there is provided a method of detecting an abnormal PPG signal, the method including: by a photoplethysmogram (PPG) sensor, emitting light to an object and detecting light scattered or reflected from the object to measure a PPG signal; by a processor, obtaining a second derivative signal of the PPG signal; by the processor, extracting a plurality of pairs of local maximum points and local minimum points from the obtained second derivative signal; by the processor, selecting at least one reference pair from among the extracted plurality of pairs of local maximum points and local minimum points; and by the processor, determining whether the PPG signal is normal by using the selected at least one reference pair.

The selecting of the at least one reference pair may include obtaining a difference between a local maximum value and a local maximum value of each pair of the plurality of extracted pairs, and selecting the reference pair based on the obtained difference between the local maximum value and the local maximum value.

The selecting of the at least one reference pair may include selecting, as a reference pair, a pair having a largest difference between the local maximum value and the local minimum value, or a pair having a largest value obtained by multiplying the obtained difference between the local maximum value and the local minimum value by a predetermined coefficient.

The determining whether the PPG signal is normal may include comparing a time value of a local maximum point of a selected reference pair with a predetermined threshold value, and based on the time value of the local maximum point being greater than the predetermined threshold value, determining that the PPG signal is abnormal.

The selecting of the at least one reference pair may include selecting a first pair and a second pair as a first reference pair and a second reference pair, respectively, from among the extracted plurality of pairs.

The determining whether the PPG signal is normal may include determining whether the PPG signal is normal by using a first amplitude of the PPG signal, which corresponds to a local minimum point of the first reference pair, and a second amplitude of the PPG signal which corresponds to a local minimum point of the second reference pair.

The determining whether the PPG signal is normal may include, based on a ratio between the first amplitude and the second amplitude being greater than a predetermined threshold value, determining that the PPG signal is abnormal.

In an aspect of an example embodiment, there is provided an apparatus for estimating bio-information, the apparatus including: a photoplethysmogram (PPG) sensor including a light source, configured to emit light to an object, and a detector, configured to detect light scattered or reflected from the object, the PPG sensor being configured to measure a PPG signal based on the detected light; and a processor configured to obtain a second derivative signal of the PPG signal, to extract a plurality of pairs of local maximum points and local minimum points from the obtained second derivative signal, and to determine whether the PPG signal is normal based on one reference pair selected from among the extracted plurality of pairs according to a first condition, and based on determining that the PPG signal is abnormal, configured to determine again whether the PPG signal is normal by using two reference pairs selected from among the extracted plurality of pairs according to a second condition.

BRIEF DESCRIPTION OF THE DRAWINGS

The above and/or other aspects will become apparent and more readily appreciated from the following description of example embodiments, taken in conjunction with the accompanying drawings.

FIG. 6 is a flowchart illustrating a method of determining whether a bio-signal is normal according to an embodiment of the disclosure.

FIG. 7 is a flowchart illustrating a method of determining whether a bio-signal is normal according to another embodiment of the disclosure.

FIG. 8 is a flowchart illustrating a method of determining whether a bio-signal is normal according to yet another embodiment of the disclosure.

Figure 1:
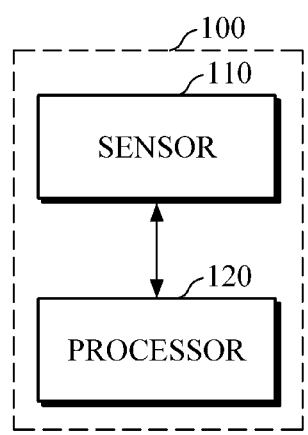
FIG. 1 is a block diagram illustrating an apparatus for estimating bio-information according to an embodiment of the disclosure.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Details of example embodiments are included in the following detailed description and drawings. Advantages and features of the disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as "unit" or "module", etc., should be understood as a unit for performing at least one function or operation and that may be embodied as hardware, software, or a combination thereof.

FIG. 1 is a block diagram illustrating an apparatus for estimating bio-information according to an embodiment of the disclosure. FIGS. 2A to 2D are diagrams explaining the principle of generating component waveforms of a photoplethysmogram (PPG) signal. FIGS. 3A and 3B are diagrams explaining examples of determining whether a PPG signal is normal.

Various embodiments of an apparatus for estimating bio-information may be implemented as an electronic device, such as a smartphone, a tablet PC, a desktop computer, a laptop computer, or various types of wearable devices, such as a wristwatch-type wearable device, a bracelet-type wearable device, a wristband-type wearable device, a ring-type wearable device, a glasses-type wearable device, a head-band-type wearable device, and the like.

Referring to FIG. 1, an apparatus 100 for estimating bio-information includes a sensor 110 and a processor 120.

The sensor 110 may measure a bio-signal from an object. For example, the bio-signal may include a photoplethysmogram (PPG) signal, an electrocardiography (ECG) signal, an electromyography (EMG) signal, an impedance plethysmogram (IPG) signal, a pressure wave signal, a video plethysmogram (VPG) signal, and the like. In this case, the object may be a body part coming into contact with or adjacent to the sensor 110, and may be a body part where pulse waves may be easily measured. For example, the object may be a skin of a wrist that is adjacent to a radial artery and an upper part of the wrist where venous blood or capillary blood passes. However, the object is not limited thereto, and may be a peripheral part of the body, such as a finger, a toe, or the like, which is a region with relatively high blood vessel density.

For example, the sensor 110 may be a PPG sensor for measuring a PPG signal from an object. The PPG sensor may include one or more light sources configured to emit light to an object and one or more detectors configured to detect light scattered or reflected from or transmitted into the object after light is emitted by the light source to the object. In this case, the light source may include a light emitting diode (LED), a laser diode (LD), a phosphor, and the like. The light source may emit light of one or more wavelengths (e.g., red, green, blue, and infrared wavelengths). The detector may include one or more photodiodes, photo transistors (PTr), image sensors (e.g., complementary metal-oxide semiconductor (CMOS) image sensor), etc., but is not limited thereto.

The processor 120 may be electrically or functionally connected to the sensor 110 and may control the sensor 110 to acquire a bio-signal. The processor 120 may analyze a waveform of the bio-signal to determine whether the bio-signal is normal, and based on the determination, the processor 120 may proceed with estimation of bio-information, or may determine an estimation failure and terminate the estimation. In this case, the bio-information may include blood pressure, arrhythmia, vascular age, skin elasticity, skin age, arterial stiffness, aortic pressure waveform, stress index, fatigue level, etc., but is not limited thereto.

Upon receiving the bio-signal from the sensor 110, the processor 120 may perform preprocessing, such as removing noise from the received signal and the like. For example, the processor 120 may perform signal correction, such as filtering (e.g., band-pass filtering between 0.4 Hz and 10 Hz), amplification of the bio-signal, converting the signal into a digital signal, smoothing, ensemble averaging of continuously measured bio-signals, and the like. In addition, the processor 120 may extract a representative waveform of one cycle from a waveform of the bio-signal, and may analyze the extracted representative waveform to determine whether the bio-signal is normal and/or to estimate bio-information. For example, the processor 120 may extract a representative waveform of one cycle by using the lowest points in the waveform of the bio-signal. In this case, the processor 120 may obtain a plurality of unit waveforms of one cycle from the waveform of the bio-signal, and may obtain the representative waveform by using any one or a combination of two or more of the plurality of unit waveforms.

Figure 2A:
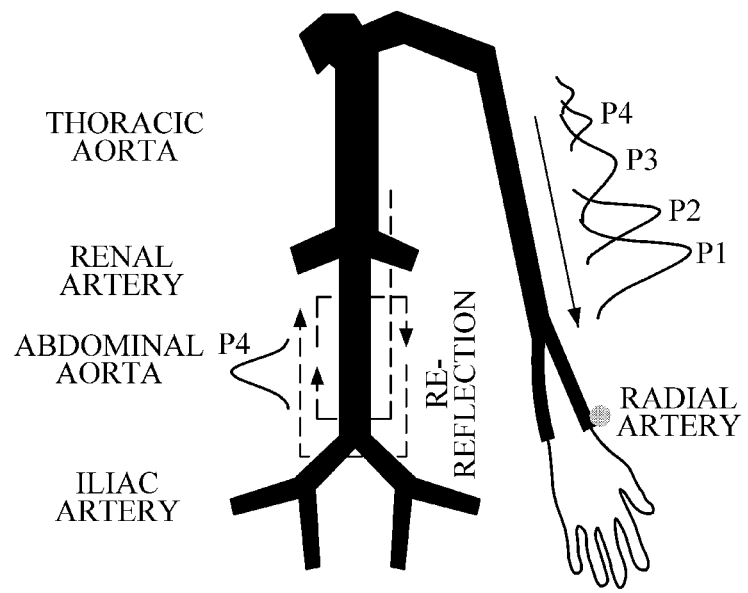
FIGS. 2A to 2D are diagrams explaining the principle of generating component waveforms of a photoplethysmogram (PPG) signal.
Figure 3A:
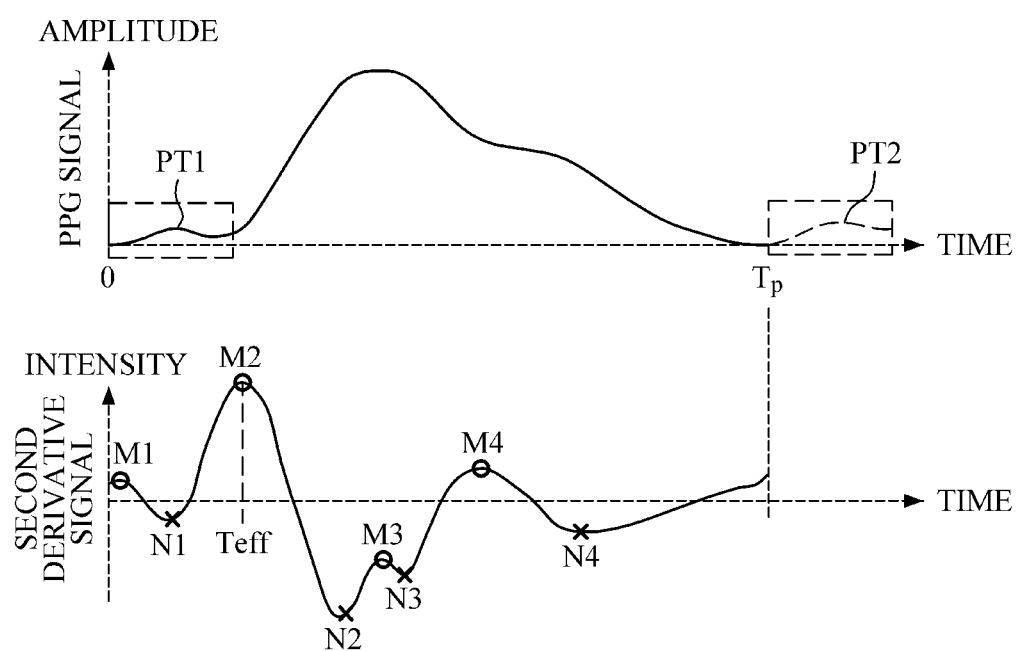
FIGS. 3A and 3B are diagrams explaining examples of determining whether a PPG signal is normal.
Figure 3B:
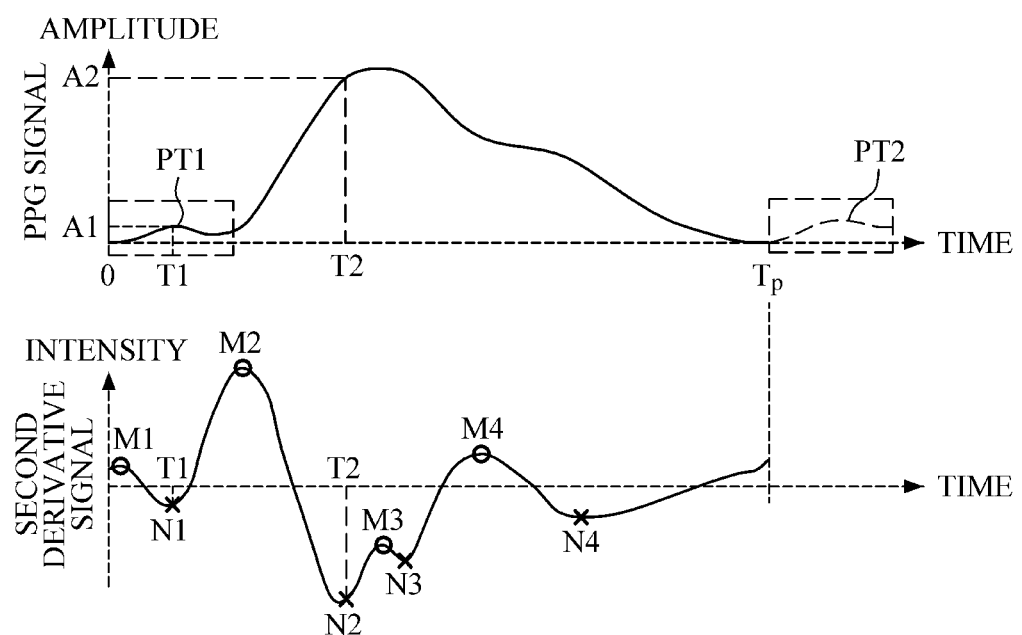

FIG. 2A is a diagram explaining the principle of generating component waveforms of a PPG signal. Referring to FIG. 2A, a PPG signal may be generally a summation of a propagation wave propagating from the heart by blood ejection from the left ventricle to peripheral parts of the body and vascular branching points, and reflection waves returning from the peripheral parts of the body or the vascular branching points. As described above, the propagation wave is related to cardiac characteristics, and the reflection waves are related to vascular characteristics. Generally, the propagation wave generated by blood ejection from the left ventricle are mainly reflected from the renal arteries and the iliac arteries to generate a first reflection wave P2 and a second reflection wave P3. As described above, the processor 120 may estimate blood pressure by dividing the waveform of the PPG signal into component waveforms P1, P2, P3, and P4 and by analyzing time values associated with the respective component waveforms P1, P2, P3, and P4 and/or amplitudes of the PPG signal.

Figure 2B:
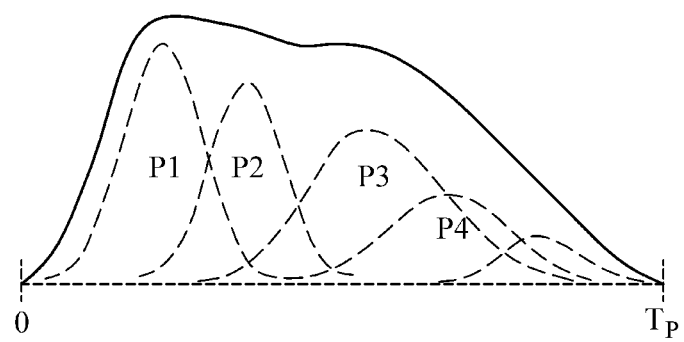
Figure 2C:
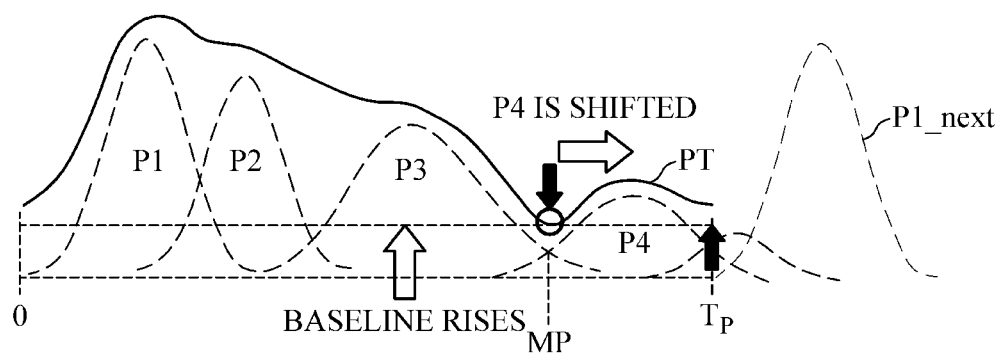

FIG. 2B is a diagram illustrating a waveform of one cycle (Tp) of a normal PPG signal measured while a user is in a sitting position. FIG. 2C is a diagram illustrating a waveform of one cycle (Tp) of an abnormal PPG signal measured while a user is in a supine position (during sleep).

Generally, as illustrated in FIG. 2B, a fourth waveform component P4 and a third waveform component P3 substantially overlap each other on a time axis in the normal PPG signal. By contrast, if a user changes from the sitting position to the supine position such as during sleep, the aorta positioned perpendicular to the heart changes to a position that is horizontal to the heart, such that hydrostatic pressure, which was applied to the aorta due to gravity resulting from a height difference from the heart, is significantly reduced or disappears. The decrease in the hydrostatic pressure physiologically leads to an increase in elasticity of the aortic vessels and decrease in diameter thereof, such that waveform components passing through the aorta in the chest and abdomen may decrease in velocity.

As illustrated in FIG. 2C, if waveform components decrease in velocity, such that a time interval between the waveform components P3 and P4 in a diastolic region gradually becomes wider, it may seem that an overlapping time interval is reduced, and an independent waveform component PT is generated. Accordingly, if the fourth waveform component P4 is shifted to a later time, a portion of the shifted fourth waveform component P4 that overlaps a first waveform component P1 next of the next periodic waveform may increase. For this reason, a start point of the systolic region of each PPG pulse may relatively rise, and a baseline of the entire PPG signal may rise.

Figure 2D:
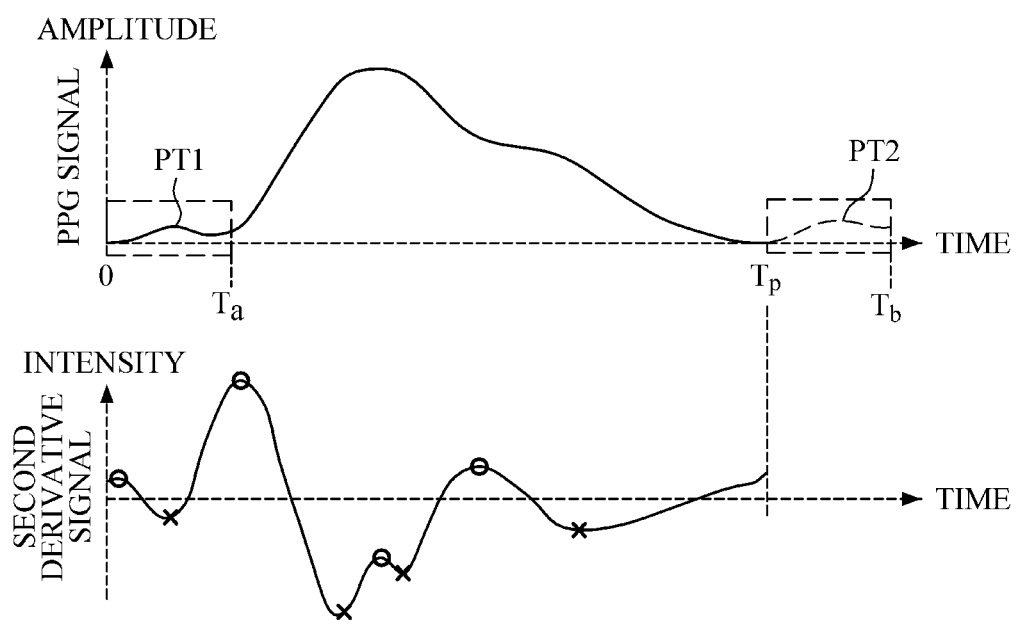

FIG. 2D is a diagram illustrating one periodic PPG signal and a second derivative signal when an abnormal waveform appears. As illustrated in FIG. 2C, if an interval between the waveform components P3 and P4 in the systolic region becomes wider, a concave point between the third waveform component P3 and the fourth waveform component P4 may be a lowest point. When one periodic signal is segmented based on the lowest point in a normal waveform, the signal is segmented as having a time interval (Ta-Tb) as one cycle. However, in the abnormal waveform, if the lowest point appears in the diastolic region, a leading edge PT1 of the waveform component, which should be included in a preceding periodic waveform, is added to the front of the current periodic waveform, and a trailing edge PT2 of the waveform component, which should be included in the current periodic waveform, is segmented as the next periodic waveform. Therefore, when an unideal PPG signal and/or unideal second derivative signal thereof is analyzed, waveform analysis may not be accurately performed, and when bio-information, e.g., blood pressure and the like, is estimated using the unideal PPG or second derivative signal, the accuracy of bio-information estimation may be reduced.

FIGS. 3A and 3B are diagrams explaining examples of determining whether a PPG signal is normal.

Upon receiving the PPG signal from the sensor 110, the processor 120 may obtain a second derivative signal by performing quadratic differential on the PPG signal. In addition, the processor 120 may extract a plurality of pairs of local maximum points and local minimum points from the obtained second derivative signal, may select at least one reference pair from among the extracted pairs of local maximum points and local minimum points, and may determine whether the PPG signal has a normal waveform by using the local maximum point and/or local minimum point of the selected reference pair.

Referring to FIG. 3A, the processor 120 may obtain a representative waveform of one cycle (0-Tp) of the PPG signal, and may obtain a second derivative signal by performing quadratic differential on the representative waveform. The processor 120 may sequentially extract pairs ((M1, N1), (M2, N2), (M3, N3), (M4, N4), . . . ) of local maximum points and local minimum points from the second derivative signal in a time sequential order. The processor 120 may select one reference pair from among the extracted pairs ((M1, N1), (M2, N2), (M3, N3), (M4, N4), . . . ) of local maximum points and local minimum points according to predetermined criteria. In this case, the processor 120 may select the reference pair by calculating a difference between the local maximum point and the local minimum point in a predetermined time interval (0 to Trange). In this case, an end point Trange of the interval may be a value based on one cycle Tp and may be, for example, Tp/2.

For example, as shown in the following Equation 1, the processor 120 may calculate the difference between the local maximum value and the local minimum value for each of the pairs and may select a pair having a largest difference as the reference pair.

$$D(n)=V_{max}(n)-V_{min}(n) \qquad \text{[Equation 1]}$$

Herein, n denotes an index of a pair of a local maximum point and a local minimum point, $V_{max}(n)$ denotes a local maximum value in an nth pair, $V_{min}(n)$ denotes a local minimum value in the nth pair, and D(n) denotes a difference between the local maximum value $V_{max}(n)$ and the local minimum value $V_{min}(n)$ in the nth pair.

In another example, as shown in Equation 2, the processor 120 may select a pair having a largest value obtained by multiplying the difference between the local maximum value and the local minimum value by a predetermined coefficient for each pair.

$$D(n)=(V_{max}(n)-V_{min}(n))\times a(n) \qquad \text{[Equation 2]}$$

Herein, n denotes an index of a pair of a local maximum point and a local minimum point, $V_{max}(n)$ denotes a local maximum value in an nth pair, $V_{min}(n)$ denotes a local minimum value in the nth pair, and a(n) denotes a coefficient for the nth pair. In this case, a(n) is a value smaller than or equal to 1, and may be defined as, for example, $(1/2)^{(n-1)}$, and D(n) denotes a result obtained by multiplying the difference between the local maximum value $V_{max}$ and the local minimum value $V_{min}$ in the nth pair by the coefficient a(n).

Upon selecting one reference pair as described above, the processor 120 may determine whether a waveform of the PPG signal is an ideal waveform by using a time value at the local maximum point of the selected reference pair. For example, as the difference between the local maximum value and the local minimum value in the second pair (M2, N2) is largest in FIG. 3A, the processor 120 may select the second pair (M2, N2) as the reference pair, and may compare a time value Teff, corresponding to the local maximum point M2 of the selected second pair (M2, N2), with a predetermined threshold value. If the time value Teff is greater than or equal to the threshold value, the processor 120 may determine that the waveform of the PPG signal is abnormal, and if not, the processor 120 may determine that the waveform of the PPG signal is normal. In this case, in consideration of a time value at which a first local maximum point generally appears in a normal waveform, the threshold value may be preset as a fixed value (e.g. 120 ms) which may be universally applied to all users, or the fixed value may be adjusted to a personalized value by performing calibration for each individual user.

Upon determining that the PPG signal is normal, the processor 120 may proceed with estimation of bio-information, and upon determining that the PPG signal is abnormal, the processor 120 may determine an estimation failure and terminate the estimation of bio-information, or may determine that the PPG signal is abnormal and proceed with the estimation of bio-information. The processor 120 may provide a user with information about the determination of the abnormal PPG signal or the estimation failure, and/or a bio-information estimation result, etc. by using an output device (e.g., display, audio output device, haptic device, etc.).

In an embodiment, during the estimation of bio-information, regardless of whether the PPG signal is normal, the processor 120 may set the selected reference pair (M2, N2) as a valid first pair in the second derivative signal, may analyze a waveform of the second derivative signal and/or the PPG signal starting from the time point Teff corresponding to the local maximum point of the set first pair, and may extract one or more features for estimating bio-information to estimate bio-information by using the extracted features. Alternatively, if the PPG signal is abnormal, the processor 120 may estimate bio-information after modifying one periodic signal by changing the sequence of an abnormal portion of the PPG signal. For example, the processor 120 may modify the current periodic signal by moving an abnormal portion (e.g., a time interval prior to the reference pair in the current periodic signal or a predetermined time interval from a start point of the current periodic signal) of the current periodic signal in the PPG signal to an interval subsequent to the current periodic signal. In another example, the processor 120 may modify the current periodic signal by deleting the abnormal portion from the current periodic signal in the PPG signal and by adding a signal of an interval, corresponding to the abnormal portion, to be subsequent to the current periodic signal, i.e., to follow a last part of the current periodic signal. However, the disclosure is not limited thereto.

Referring to FIG. 3B, the processor 120 may obtain a representative waveform of one cycle (0 to Tp) of the PPG signal, and may obtain a second derivative signal by performing quadratic differential on the representative waveform. The processor 120 may sequentially extract pairs ((M1, N1), (M2, N2), (M3, N3), (M4, N4), . . . ) of local maximum points and local minimum points from the second derivative signal in a time sequential order. The processor 120 may select two reference pairs from among the extracted pairs ((M1, N1), (M2, N2), (M3, N3), (M4, N4), . . . ) of local maximum points and local minimum points according to predetermined criteria. For example, the processor 120 may select a first pair as a first reference pair and a second pair as a second reference pair. However, the processor 120 is not limited thereto, and may select the first and second reference pairs by various methods. For example, the processor 120 may select the reference pair, in the manner as described in the example of FIG. 3A, as the second reference pair, and select a pair preceding the selected pair as the first reference pair.

In the case where the processor 120 selects the first pair (M1, N1) and the second pair (M2, N2) in the second derivative signal as the first reference pair and the second reference pair, respectively, the processor 120 may determine whether the PPG signal is normal by using a local minimum point N1 of the first reference pair and a local minimum point N2 of the second reference pair. For example, the processor 120 may compare a ratio A2/A1 between an amplitude A1, corresponding to a time value T1 of the local minimum point N1 in the first reference pair of the PPG signal, and an amplitude A2, corresponding to a time value T2 of the local minimum point N2 in the second reference pair of the PPG signal, with a predetermined threshold value (e.g., 10), and if the ratio (A2/A1) is greater than or equal to the threshold value, the processor 120 may determine that the PPG signal is abnormal, and if not, the processor 120 may determine that the PPG signal is normal. In this case, the threshold value may be preset based on performance of the apparatus, accuracy in estimating bio-information, and the like.

Upon determining that the PPG signal is normal, the processor 120 may proceed with estimation of bio-information, and upon determining that the PPG signal is abnormal, the processor 120 may determine an estimation failure and terminate the estimation of bio-information or may determine that the PPG signal is abnormal and proceed with the estimation of bio-information. The processor 120 may provide a user with information about the determination of the abnormal PPG signal or the estimation failure, and/or a bio-information estimation result, etc. by using an output device (e.g., display, audio output device, haptic device, etc.).

During the estimation of bio-information, the processor 120 may set the first reference pair or the second reference pair as a valid first pair in the second derivative signal, and may estimate bio-information by analyzing a waveform starting from the valid first pair in the second derivative signal and/or the PPG signal. In this case, a condition for setting the valid first pair may be predetermined. For example, if the PPG signal is normal, the processor 120 may unconditionally set the first reference pair as the valid first pair. Alternatively, even when the ratio (A2/A1) is within a normal range, if the ratio is greater than or equal to a predetermined level, the processor 120 may set the second reference pair as the valid first pair. In yet another example, if the PPG signal is abnormal, the processor 120 may set the second reference pair as the valid first pair. Alternatively, as described above, if the PPG signal is abnormal, the processor 120 may estimate bio-information after modifying the periodic signal by changing the sequence of an abnormal portion of the PPG signal.

The processor 120 may determine whether the bio-signal is abnormal based on both the embodiments of FIGS. 3A and 3B. For example, first based on the embodiment of FIG. 3A, the processor 120 may determine whether the bio-signal is abnormal, and upon determining that the bio-signal is abnormal, the processor 120 may determine again whether the bio-signal is abnormal based on the embodiment of FIG. 3B. Upon determining that the bio-signal is abnormal in both the first and second determination processes according to the embodiments of FIGS. 3A and 3B, the processor 120 may finally determine an estimation failure and terminate the estimation of bio-information, and upon determining that the bio-signal is normal in the second determination process, the processor 120 may proceed with the estimation of bio-information.

During the estimation of bio-information, for example, blood pressure, based on the above determination result, the processor 120 may extract one or more features associated with blood pressure by analyzing a waveform starting from a point at which the valid first pair is set in the second derivative signal.

Generally, it is known that a variation in mean arterial pressure (MAP) is proportional to cardiac output (CO) and total peripheral resistance (TPR), as shown in the following Equation 3.

$$\Delta MAP = CO \times TPR \qquad \text{[Equation 3]}$$

Herein, ΔMAP denotes a difference in MAP between a left ventricle and a right atrium, in which MAP of the right atrium is generally in a range of 3 mmHg to 5 mmHg, such that the MAP in the right atrium is similar to MAP in the left ventricle or MAP of the upper arm. If absolute actual CO and TPR values are known, MAP may be obtained from the aorta or the upper arm. However, it may be difficult to estimate absolute CO and TPR values based on a PPG signal. Accordingly, the blood pressure variation may be obtained using a feature associated with the CO (hereinafter referred to as a CO feature) or a feature associated with the TPR (hereinafter referred to as a TPR feature). Here, the CO feature may be a feature value which shows an increasing/decreasing trend in proportion to an actual CO value which relatively increases/decreases when an actual TPR value does not change significantly compared to a resting state. Further, the TPR feature may be a feature value which shows an increasing/decreasing trend in proportion to an actual TPR value which relatively increases/decreases when an actual CO value does not change significantly compared to a resting state.

The processor 120 may extract the CO feature and the TPR feature from the PPG signal and/or the second derivative signal. For example, the processor 120 may extract heart rate (HR) as the CO feature from the PPG signal. In addition, when time values at the local minimum points of the valid first pair and the second pair in the second derivative signal are defined as T1 and T2 respectively, and amplitude values corresponding to the time values T1 and T2 are defined as P1 and P2 respectively, the processor 120 may extract a ratio (P2/P1) between the amplitude values, corresponding to the time values T1 and T2, as the TPR feature. However, the features are not limited thereto, and the processor 120 may extract, for example, time values of the respective waveform components in the second derivative signal, a time value and an amplitude value of a point at which an amplitude has a maximum value in a systolic region of the PPG signal, a time value and an amplitude value of a point at which a slope of the PPG signal is closest to zero in the systolic region, a time value and an amplitude value of an internally dividing point between time values of adjacent waveform components in the second derivative signal, and a value obtained by using one or an appropriate combination of two or more of a total or partial area of the PPG signal, duration, cycle, and pulse pressure as the CO feature and/or the TPR feature from the second derivative signal.

Upon extracting the CO feature and/or the TPR feature, the processor 120 may estimate blood pressure by using a predefined blood pressure estimation model. The processor 120 may further obtain features in addition to the CO feature and the TPR feature, and may obtain a final blood pressure value by inputting the respective feature values to the blood pressure estimation model. In this case, the blood pressure estimation model may be a model that defines a correlation between the feature values and the blood pressure and may be defined as a linear and/or nonlinear equation(s).

The processor 120 may compare blood pressure, which is estimated during sleep, with blood pressure estimated in a normal posture rather than during sleep. In addition, based on the comparison, the processor 120 may predict a variety of information associated with cardiovascular diseases. For example, if the blood pressure during sleep does not fall by a threshold value or more compared to a blood pressure level during non-sleep or if the blood pressure during sleep is not within a normal blood pressure range, the processor 120 may guide (e.g., notify or output related information) a user on the risk of developing cardiovascular diseases, such as thrombosis, orthostatic hypotension, and the like.

Figure 4:
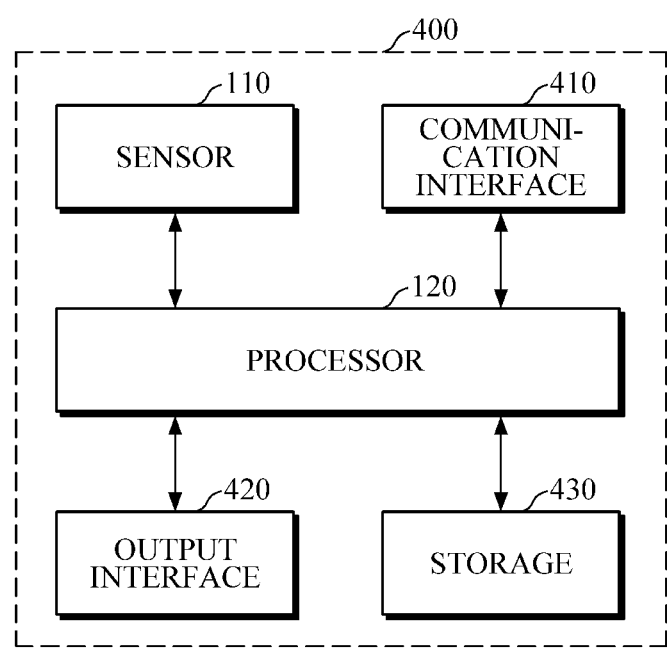
FIG. 4 is a block diagram illustrating an apparatus for estimating bio-information according to another embodiment of the disclosure.
Figure 5A:
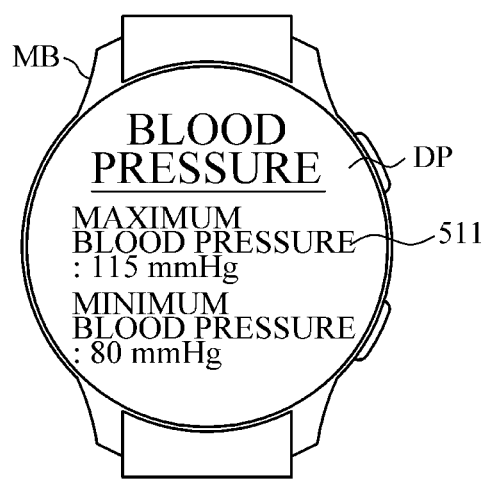
FIGS. 5A to 5C are diagrams illustrating an example of providing information related to estimating blood pressure by an electronic device.
Figure 5B:
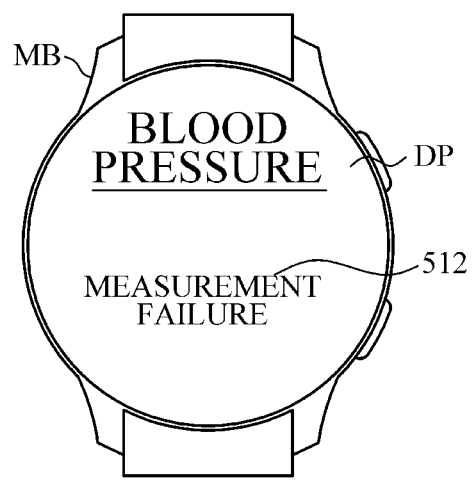
Figure 5C:
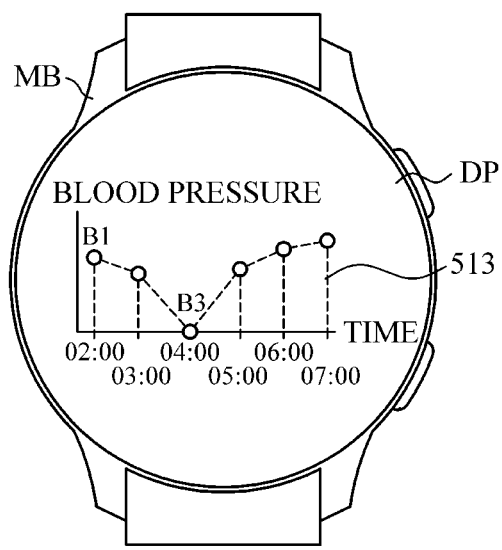

FIG. 4 is a block diagram illustrating an apparatus for estimating bio-information according to another embodiment of the disclosure. FIGS. 5A to 5C are diagrams illustrating an example of providing information related to estimating blood pressure by an electronic device.

Referring to FIG. 4, an apparatus 400 for estimating bio-information includes the sensor 110, the processor 120, a communication interface 410, an output interface 420, and a storage 430. The sensor 110 and the processor 120 are described in detail above, such that a description thereof will be omitted.

The communication interface 410 may be electrically connected to the processor 120 and may communicate with another electronic device under the control of the processor 120 to transmit and receive data, such as reference blood pressure, blood pressure estimation model, information as to whether a bio-signal is normal, blood pressure estimation result, etc., by using various communication techniques. Another electronic device may include a blood pressure measuring device such as a cuff sphygmomanometer, a smartphone, a tablet PC, a desktop computer, a laptop computer, and the like. However, the electronic device is not limited thereto. In this case, the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, 3G, 4G, and 5G communications, and the like. However, the communication techniques are not limited thereto.

The output interface 420 may output processing results of the sensor 110 and/or the processor 120 and may provide the results to a user. The output interface 420 may provide the user with information by various visual and/or non-visual methods using, for example, a visual output module such as a display, an audio output module such as a speaker, and/or a haptic module using vibrations, tactile sensation, and the like.

For example, referring to FIGS. 5A and 5B, if blood pressure is normally estimated, the output interface 420 may display a blood pressure estimation result 511 on a display DP disposed on a main body MB of the apparatus 400. In addition, if the processor 120 determines that a PPG signal is abnormal, the output interface 420 may output information about the determination of the abnormal PPG signal, e.g., a text such as "your PPG signal is abnormal." Further, if the processor 120 determines an estimation failure, the output interface 420 may output a text 512, such as "measurement failure," as illustrated in FIG. 5B. Moreover, as illustrated in FIG. 5C, if the PPG signal is automatically measured every hour during sleep at night, the output interface 420 may display a measurement result in a visual graph 513. In this case, if a user selects a graphic object B1 on the graph 513, the output interface 420 may display a blood pressure estimation result at a corresponding time (e.g., 2:00 a.m.) as illustrated in FIG. 5A, and if the user selects a graphic object B3, the output interface 420 may display information about a measurement failure at a corresponding time (e.g., 4:00 a.m.) as illustrated in FIG. 5B. However, these examples are merely for convenience of explanation, and the output interface 420 is not limited thereto.

The storage 430 may store data related to operations of the sensor 110 and/or the processor 120, and/or the processing results of the sensor 110 and/or the processing results of the processor 120. For example, the storage 430 may store a blood pressure estimation model, criteria for determining whether the PPG signal is normal, a threshold value, user characteristics (e.g., gender, age, health condition, etc.), a bio-signal, a feature value, a reference blood pressure, an estimated blood pressure value, and the like.

In this case, the storage 430 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

FIG. 6 is a flowchart illustrating a method of determining whether a bio-signal is normal according to an embodiment of the disclosure. The method of determining whether the bio-signal is normal in FIG. 6 may be performed by any one of the aforementioned apparatuses 100 and 400 for estimating bio-information.

First, the apparatus for estimating bio-information may receive an input of a bio-signal in 610. In this case, by using a sensor, the apparatus for estimating bio-information may emit light to an object and detect light scattered or reflected from the object to measure a bio-signal. However, the apparatus for estimating bio-information is not limited thereto, and may receive, from another electronic device, a bio-signal measured from an object. The apparatus for estimating bio-information may perform preprocessing such as removing noise from the input bio-signal and the like.

Then, the apparatus for estimating bio-information may obtain a second derivative signal by performing quadratic differential on the bio-signal in 620. In this case, the apparatus for estimating bio-information may obtain a representative waveform of one cycle based on a minimum point of the waveform of the bio-signal, and may perform quadratic differential on the representative waveform.

Subsequently, the apparatus for estimating bio-information may extract a plurality of pairs of (local maximum points, local minimum points) from the waveform of the second derivative signal in 630. In this case, the apparatus for estimating bio-information may sequentially extract the pairs of (local maximum points, local minimum points) from the waveform of the second derivative signal in a time sequential order.

Next, the apparatus for estimating bio-information may select one reference pair for use in determining whether the bio-signal is normal from among the plurality of pairs of (local maximum points, local minimum points) in 640. For example, the apparatus for estimating bio-information may select, as the reference pair, a pair having a largest value obtained by subtracting a local minimum value from a local maximum value of each pair in a predetermined time interval, or a pair having a largest value obtained by multiplying the value, obtained by subtracting the local minimum value from the local maximum value of each pair, by a predetermined coefficient.

Then, the apparatus for estimating bio-information may compare a time value of the local maximum point of the selected reference pair with a threshold value in 650. Upon comparison, if the time value of the local maximum point in the reference pair is greater than or equal to the threshold value, the apparatus for estimating bio-information may determine that a waveform of the bio-signal is abnormal in 660, and if not, the apparatus for estimating bio-information may determine that the waveform of the bio-signal is normal in 670. If the waveform of the bio-signal is normal, the apparatus for estimating bio-information may proceed with estimation of bio-information, and if the waveform of the bio-signal is abnormal, the apparatus for estimating bio-information may determine an estimation failure and may terminate the estimation of bio-information, or may determine that the waveform of the bio-signal is abnormal and may proceed with the estimation of bio-information.

FIG. 7 is a flowchart illustrating a method of determining whether a bio-signal is normal according to another embodiment of the disclosure. The method of determining whether the bio-signal is normal in FIG. 7 may be performed by any one of the aforementioned apparatuses 100 and 400 for estimating bio-information.

First, the apparatus for estimating bio-information may receive an input of a bio-signal in 710. In this case, the apparatus for estimating bio-information may receive a bio-signal from a sensor or may receive, from another electronic device, a bio-signal measured from an object. The apparatus for estimating bio-information may perform pre-processing such as removing noise from the input bio-signal.

Then, the apparatus for estimating bio-information may obtain a second derivative signal by performing quadratic differential on the bio-signal in 720. In this case, the apparatus for estimating bio-information may obtain a representative waveform of one cycle based on a minimum point of the waveform of the bio-signal, and may perform quadratic differential on the representative waveform.

Subsequently, the apparatus for estimating bio-information may extract a plurality of pairs of (local maximum points, local minimum points) from the waveform of the second derivative signal in 730. In this case, the apparatus for estimating bio-information may sequentially extract the pairs of (local maximum points, local minimum points) from the waveform of the second derivative signal in a time sequential order.

Next, the apparatus for estimating bio-information may select two reference pairs for use in determining whether the bio-signal is normal from among the plurality of pairs of (local maximum points, local minimum points) in 740. For example, the apparatus for estimating bio-information may obtain first and second pairs as the reference pairs in a predetermined time interval.

Then, the apparatus for estimating bio-information may compare a ratio between amplitude values of the PPG signal, which respectively correspond to the time values of the local minimum points of the selected reference pairs, with a threshold value in 750. Upon comparison, if the ratio between the amplitude values of the reference pairs is greater than or equal to the threshold value, the apparatus for estimating bio-information may determine that a waveform of the bio-signal is abnormal in 760, and if not, the apparatus for estimating bio-information may determine that the waveform of the bio-signal is normal in 770. If the waveform of the bio-signal is normal, the apparatus for estimating bio-information may proceed with estimation of bio-information, and if the waveform of the bio-signal is abnormal, the apparatus for estimating bio-information may determine an estimation failure and may terminate the estimation of bio-information, or may determine that the waveform of the bio-signal is abnormal and may proceed with the estimation of bio-information.

FIG. 8 is a flowchart illustrating a method of determining whether a bio-signal is normal according to yet another embodiment of the disclosure. The method of determining whether the bio-signal is normal in FIG. 8 may be performed by any one of the aforementioned apparatuses 100 and 400 for estimating bio-information.

First, the apparatus for estimating bio-information may receive an input of a bio-signal in 810 and may obtain a second derivative signal by performing quadratic differential on the input bio-signal in 820. Then, the apparatus for estimating bio-information may extract a plurality of pairs of (local maximum points, local minimum points) from the waveform of the second derivative signal in 830 and may select one reference pair from among the plurality of pairs of (local maximum points, local minimum points) according to a first condition in 840. For example, the first condition may be a condition for selecting a pair having a largest value, obtained by subtracting a local minimum value from a local maximum value of each pair in a predetermined time interval, or a pair having a largest value obtained by multiplying the value, obtained by subtracting the local minimum value from the local maximum value of each pair, by a predetermined coefficient.

Then, the apparatus for estimating bio-information may compare a time value of the local maximum point of the selected reference pair with a threshold value (e.g., a first threshold value) in 850. Upon comparison, if the time value of the local maximum point of the reference pair is greater than or equal to the threshold value, the apparatus for estimating bio-information may select again two reference pairs according to a second condition in 860, and may compare a ratio between amplitude values of the PPG signal, which correspond to the time values of the local minimum points of the selected reference pairs, with a threshold value (e.g., a second threshold value) in 870. Upon comparison, if the ratio between the amplitude values of the reference pairs is greater than or equal to the threshold value, the apparatus for estimating bio-information may determine that a waveform of the bio-signal is abnormal in 880. If the time value of the local maximum point of the reference pair is smaller than the threshold value (e.g., the first threshold value) upon comparison in 850, or if the ratio between the amplitude values of the reference pairs is smaller than the threshold value (e.g., the second threshold value) in 870, the apparatus for estimating bio-information may determine that the waveform of the bio-signal is normal in 890.

Figure 9:
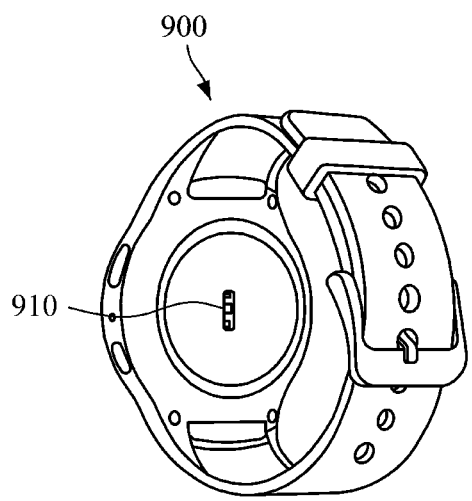
FIGS. 9 to 11 are diagrams illustrating various structures of an electronic device including an apparatus for estimating bio-information.
Figure 10:
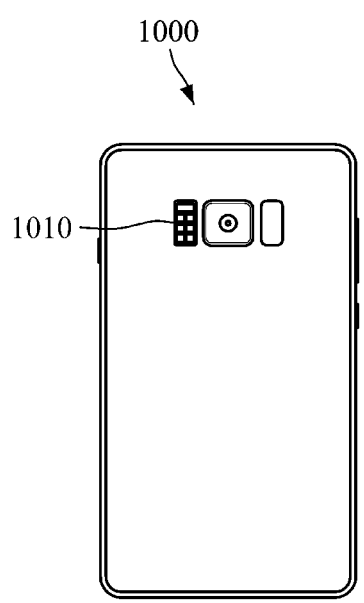
Figure 11:
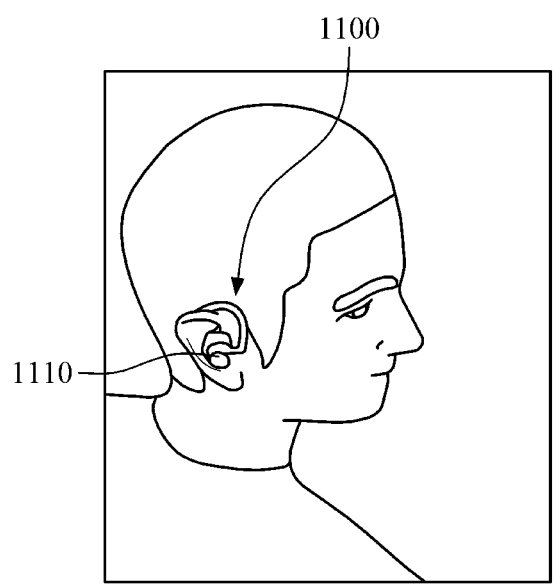

FIGS. 9 to 11 are diagrams illustrating various structures of an electronic device including an apparatus for estimating bio-information.

The electronic device may include, for example, various types of wearable devices, e.g., a smart watch, a smart band, smart glasses, smart earphones, a smart ring, a smart patch, and a smart necklace, and a mobile device such as a smartphone, a tablet PC, etc., or home appliances or various Internet of Things (IoT) devices (e.g., home IoT device, etc.) based on Internet of Things (IoT) technology.

The electronic device may include a sensor device, a processor, an input device, a communication module, a camera module, an output device, a storage device, and a power module. All the components of the electronic device may be integrally mounted in a specific device or may be distributed in two or more devices. The sensor device may include the sensor (e.g., PPG sensor) of the apparatuses 100 and 400 for estimating bio-information, and may further include an additional sensor, such as a gyro sensor, a Global Positioning System (GPS), and the like.

The processor may execute programs, stored in the storage device, to control components connected to the processor, and may perform various data processing or computation, including estimation of bio-information. The processor may include a main processor, e.g., a central processing unit (CPU) or an application processor (AP), etc., and an auxiliary processor, e.g., a graphics processing unit (GPU), an image signal processor (ISP), a sensor hub processor, or a communication processor (CP), etc., which is operable independently from, or in conjunction with, the main processor.

The input device may receive a command and/or data to be used by each component of the electronic device, from a user and the like. The input device may include, for example, a microphone, a mouse, a keyboard, or a digital pen (e.g., a stylus pen, etc.).

The communication module may support establishment of a direct (e.g., wired) communication channel and/or a wireless communication channel between the electronic device and other electronic device, a server, or the sensor device within a network environment, and performing; of communication via the established communication channel. The communication module may include one or more communication processors that are operable independently from the processor and supports a direct communication and/or a wireless communication. The communication module may include a wireless communication module, e.g., a cellular communication module, a short-range wireless communication module, or a global navigation satellite system (GNSS) communication module, etc., and/or a wired communication module, e.g., a local area network (LAN) communication module, a power line communication (PLC) module, and the like. These various types of communication modules may be integrated into a single chip, or may be separately implemented as multiple chips. The wireless communication module may identify and authenticate the electronic device in a communication network by using subscriber information (e.g., international mobile subscriber identity (MIST), etc.) stored in a subscriber identification module.

The camera module may capture still images or moving images. The camera module may include a lens assembly having one more lenses, image sensors, image signal processors, and/or flashes. The lens assembly included in the camera module may collect light emanating from a subject to be imaged.

The output device may visually and/or non-visually output data (e.g., estimated blood pressure values, health condition, warning, actions, etc.) generated or processed by the electronic device. The output device may include a sound output device, a display device, an audio module, and/or a haptic module.

The sound output device may output sound signals to the outside of the electronic device. The sound output device may include a speaker and/or a receiver. The speaker may be used for general purposes, such as playing multimedia or playing record, and the receiver may be used for incoming calls. The receiver may be implemented separately from, or as part of, the speaker.

The display device may visually provide information to the outside of the electronic device. The display device may include, for example, a display, a hologram device, or a projector and control circuitry to control the devices. The display device may include touch circuitry adapted to detect a touch, and/or sensor circuitry (e.g., pressure sensor, etc.) adapted to measure the intensity of force incurred by the touch.

The audio module may convert a sound into an electrical signal or vice versa. The audio module may obtain the sound via the input device, or may output the sound via the sound output device, and/or a speaker and/or a headphone of another electronic device directly or wirelessly connected to the electronic device.

The haptic module may convert an electrical signal into a mechanical stimulus (e.g., vibration, motion, etc.) or electrical stimulus which may be recognized by a user by tactile sensation or kinesthetic sensation. The haptic module may include, for example, a motor, a piezoelectric element, and/or an electric stimulator.

The storage device may store driving conditions required for driving the sensor device, and various data required for other components of the electronic device. The various data may include, for example, software and input data and/or output data for a command related thereto. The storage device may include a volatile memory and/or a non-volatile memory.

The power module may manage power supplied to the electronic device. The power module may be implemented as part of, for example, a power management integrated circuit (MIC). The power module may include a battery, which may include a primary cell which is not rechargeable, a secondary cell which is rechargeable, and/or a fuel cell.

Referring to FIG. 9, the electronic device may be implemented as a wristwatch wearable device 900, and may include a main body and a wrist strap. A display is provided on a front surface of the main body, and may display various application screens, including time information, received message information, and the like. A sensor device 910 may be disposed on a rear surface of the main body.

Referring to FIG. 10, the electronic device may be implemented as a mobile device 1000 such as a smartphone. The mobile device 1000 may include a housing and a display panel. The housing may form an exterior of the mobile device 1000. The housing has a first surface, on which a display panel and a cover glass may be disposed sequentially, and the display panel may be exposed to the outside through the cover glass. A sensor device 1010, a camera module and/or an infrared sensor, and the like may be disposed on a second surface of the housing. The processor and various other components may be disposed in the housing.

Referring to FIG. 11, the electronic device may be implemented as an ear-wearable device 1100. The ear-wearable device 1100 may include a main body and an ear strap. A user may wear the ear-wearable device 1100 by hanging the ear strap on the auricle. The ear strap may be omitted depending on a shape of the ear-wearable device 1100. The main body may be inserted into the external auditory meatus. A sensor device 1110 may be mounted in the main body. Further, the processor may be disposed in the main body, and may estimate blood bio-information by using a PPG signal measured by the sensor device 1110. Alternatively, the ear-wearable device 1100 may estimate bio-information by interworking with an external device. For example, the ear-wearable device 1100 may transmit the PPG signal, measured by the sensor device 1110 of the ear-wearable device 1100, to an external device, e.g., a smartphone, a tablet PC, etc., through a communication module provided in the main body, so that a processor of the external device may estimate bio-information, and may output the estimated bio-information value through a sound output module provided in the main body of the ear-wearable device 1100.

The disclosure may be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium may be distributed over a plurality of computer systems connected to a network so that a computer-readable code is written thereto and executed therefrom in a decentralized manner. Functional programs, codes, and code segments related to implementing the disclosure may be readily deduced by programmers of ordinary skill in the art to which the disclosure pertains.

The disclosure has been described herein with regard to example embodiments. However, it will be obvious to those skilled in the art that various changes and modifications may be made without changing technical conception and essential features of the disclosure. Thus, it is clear that the above-described embodiments are illustrative in all aspects and are not intended to limit the disclosure.

What is claimed is:

1. An apparatus for estimating bio-information, the apparatus comprising:
 a photoplethysmogram (PPG) sensor having a light source, configured to emit light toward an object, and a detector, configured to detect light scattered or reflected from the object, the PPG sensor being configured to measure a PPG signal based on the detected light; and
 a processor configured to obtain a second derivative signal of the PPG signal, configured to extract a plurality of pairs of local maximum points and local minimum points from the obtained second derivative signal, configured to select at least one reference pair from among the extracted plurality of pairs, and configured to determine whether the PPG signal is normal by using the selected at least one reference pair,
 wherein the processor is configured to sequentially extract the plurality of pairs of local maximum points and local minimum points from the second derivative signal in a time sequential order,
 wherein the processor is configured to obtain a difference between a local maximum value and a local minimum value of each pair of the extracted plurality of pairs, and select the at least one reference pair based on the obtained difference between the local maximum value and the local minimum value,
 wherein the processor is configured to select, as a reference pair, a pair having a largest difference between the local maximum value and the local minimum value, or a pair having a largest value obtained by multiplying the obtained difference between the local maximum value and the local minimum value by a predetermined coefficient, and
 wherein the processor is configured to compare a time value of a local maximum point of a selected reference pair with a predetermined threshold value, and based on the time value of the local maximum point being greater than the predetermined threshold value, the processor is configured to determine that the PPG signal is abnormal.

2. The apparatus of claim 1, wherein:
 based on a determination that the PPG signal is normal, the processor is configured to estimate bio-information by using the PPG signal, the bio-information including a blood pressure; and
 based on a determination that the PPG signal is abnormal, the processor is configured to determine an estimation failure and terminate estimation of bio-information, or configured to estimate the bio-information after modifying one periodic signal of the PPG signal determined as abnormal, or configured to estimate the bio-information after setting a pair from the selected at least one reference pair as a first pair that is valid for the second derivative signal.

3. The apparatus of claim 2, further comprising an output interface configured to output at least one of a result of the estimation of the bio-information or information about the estimation failure.

4. The apparatus of claim 1, wherein the processor is configured to select the at least one reference pair within a predetermined time period which is set based on one cycle of the PPG signal.

5. The apparatus of claim 1, wherein based on a determination that the PPG signal is normal, the processor is configured to set the reference pair as a first pair that is valid for the second derivative signal, and estimate the bio-information by using at least one of the second derivative signal or the PPG signal.

6. The apparatus of claim 1, wherein the processor is configured to select a first pair and a second pair as a first reference pair and a second reference pair, respectively, from among the extracted plurality of pairs.

7. The apparatus of claim 6, wherein the processor is configured to, by using a first amplitude of the PPG signal, which corresponds to a local minimum point of the first reference pair, and a second amplitude of the PPG signal which corresponds to a local minimum point of the second reference pair, determine whether the PPG signal is normal.

8. The apparatus of claim 7, wherein the processor is configured to, based on a ratio between the first amplitude and the second amplitude being greater than a predetermined threshold value, determine that the PPG signal is abnormal.

9. A method of detecting an abnormal photoplethysmogram (PPG) signal, the method comprising:
 emitting, by a PPG sensor, light toward an object and detecting light scattered or reflected from the object to measure a PPG signal;
 obtaining, by a processor, a second derivative signal of the PPG signal;
 extracting, by the processor, a plurality of pairs of local maximum points and local minimum points from the obtained second derivative signal;
 selecting, by the processor, at least one reference pair from among the extracted plurality of pairs of local maximum points and local minimum points; and
 determining, by the processor, whether the PPG signal is normal by using the selected at least one reference pair,
 wherein the selecting of the at least one reference pair comprises obtaining a difference between a local maximum value and a local minimum value of each pair of the extracted plurality of pairs, and selecting the at least one reference pair based on the obtained difference between the local maximum value and the local minimum value, wherein the selecting of the at least one reference pair comprises selecting, as a reference pair, a pair having a largest difference between the local maximum value and the local minimum value, or a pair having a largest value obtained by multiplying the obtained difference between the local maximum value and the local minimum value by a predetermined coefficient, wherein the determining whether the PPG signal is normal comprises comparing a time value of a local maximum point of a selected reference pair with a predetermined threshold value, and in response to the time value of the local maximum point being greater than the predetermined threshold value, determining that the PPG signal is abnormal, and wherein the extracting a plurality of pairs of local maximum points and local minimum points comprises sequentially extracting the plurality of pairs of local maximum points and local minimum points from the second derivative signal in a time sequential order.

10. The method of claim 9, wherein the selecting of the at least one reference pair comprises selecting a first pair and a second pair as a first reference pair and a second reference pair, respectively, from among the extracted plurality of pairs.

11. The method of claim 10, wherein the determining whether the PPG signal is normal comprises determining whether the PPG signal is normal by using a first amplitude of the PPG signal, which corresponds to a local minimum point of the first reference pair, and a second amplitude of the PPG signal which corresponds to a local minimum point of the second reference pair.

12. The method of claim 11, wherein the determining whether the PPG signal is normal comprises, in response to a ratio between the first amplitude and the second amplitude being greater than a predetermined threshold value, determining that the PPG signal is abnormal.

* * * * *